United States Patent
Song et al.

(10) Patent No.: US 8,288,171 B2
(45) Date of Patent: Oct. 16, 2012

(54) BIOCHIP AND APPARATUS FOR DETECTING BIOMATERIAL USING BIOCHIP

(75) Inventors: Hyun-Woo Song, Daejeon (KR); Yo Han Choi, Daejeon (KR); Hyeon-Bong Pyo, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 477 days.

(21) Appl. No.: 12/484,806

(22) Filed: Jun. 15, 2009

(65) Prior Publication Data
US 2010/0159614 A1 Jun. 24, 2010

(30) Foreign Application Priority Data
Dec. 22, 2008 (KR) .................. 10-2008-0130958

(51) Int. Cl.
*G01N 33/566* (2006.01)
(52) U.S. Cl. ........................................ 436/501
(58) Field of Classification Search .................. None
See application file for complete search history.

(56) References Cited

U.S. PATENT DOCUMENTS

| | | | |
|---|---|---|---|
| 5,552,272 A * | 9/1996 | Bogart | 435/6.12 |
| 5,633,724 A * | 5/1997 | King et al. | 356/445 |
| 5,763,189 A | 6/1998 | Buechler et al. | |
| 5,834,318 A * | 11/1998 | Buettner | 436/518 |
| 6,500,679 B2 | 12/2002 | Akimoto et al. | |
| 6,830,731 B1 | 12/2004 | Buechler et al. | |
| 7,141,378 B2 | 11/2006 | Miller et al. | |
| 7,943,395 B2 * | 5/2011 | Wei et al. | 436/514 |
| 2004/0076948 A1 | 4/2004 | Pettersson | |
| 2004/0241462 A1 | 12/2004 | Lee et al. | |
| 2005/0130226 A1 * | 6/2005 | Ahn et al. | 435/7.1 |
| 2006/0003320 A1 * | 1/2006 | Miller et al. | 435/5 |
| 2006/0147954 A1 | 7/2006 | Laitala et al. | 435/6 |
| 2007/0037231 A1 * | 2/2007 | Sauer-Budge et al. | 435/7.32 |
| 2009/0117006 A1 * | 5/2009 | Fernandez | 422/82.08 |

FOREIGN PATENT DOCUMENTS

| | | |
|---|---|---|
| EP | 1 742 054 | 1/2007 |
| EP | 1 742 054 A1 | 1/2007 |
| EP | 1903330 A2 | 3/2008 |
| JP | 02-066430 A | 3/1990 |
| JP | 11083857 A | 3/1999 |
| JP | 11-199867 A | 7/1999 |
| JP | 2002-508837 A | 3/2002 |

(Continued)

OTHER PUBLICATIONS

L. Lévesque et al., "Precise thickness and refractive index determination of polyimide films using attenuated total reflection," Applied Optics, Dec. 1, 1994, pp. 8036-8040, vol. 33, No. 34.

(Continued)

*Primary Examiner* — N. C. Yang
*Assistant Examiner* — Richard Moerschell

(57) ABSTRACT

Provided is a biochip and an apparatus for detecting a biomaterial. The biochip includes a metal thin film on the surface of a substrate, restraining autofluorescence of the substrate, and a spacer on the metal thin film, having capture molecules immobilized on the surface of the spacer and specifically bound to target molecules. The spacer has a thickness controlled to enhance the strength of a fluorescence signal emitted from a fluorophore labeled with the target molecules and immobilized on the spacer by the specific binding between the capture molecule and the target molecule.

19 Claims, 9 Drawing Sheets

FOREIGN PATENT DOCUMENTS

| | | |
|---|---|---|
| JP | 2002-286639 A | 10/2002 |
| JP | 2007-003363 A | 1/2007 |
| JP | 2007-240361 A | 9/2007 |
| KR | 1020040104046 A | 12/2004 |
| KR | 1020080086091 A | 9/2008 |
| WO | WO 98/53304 | * 11/1998 |
| WO | WO 98/53304 A1 | 11/1998 |
| WO | WO 2007/105771 A1 | 9/2007 |

OTHER PUBLICATIONS

K.H.Drexhage, "Influence of a Dielectric Interface on Fluorescence Decay Time," Journal of Luminescence, 1970, pp. 693-701, Issue I.2.

Katri Kuningas et al., "Upconversion Fluorescence Resonance Energy Transfer in a Homogeneous Immunoassay for Estradiol," Analytical Chemistry, Jul. 1, 2006, pp. 4690-4696, vol. 78, No. 13.

R.P.H. Kooyman et al., "Surface Plasmon Resonance Immunosensors: Sensitivity Considerations," Analytica Chimica Acta, 1988, pp. 35-45, Issue 213.

Scott W. Corzine et al., "Design of Fabry-Perot Surface-Emitting Lasers with a Periodic Gain Structure," IEEE Journal of Quantum Electronics, Jun. 1989, pp. 1513-1524, vol. 25, No. 6.

Minyung Lee et al., "Fluorescence quenching and lifetime distributions of single molecules on glass surfaces," Chemical Physics Letters, Jun. 27, 2002, pp. 412-419, Issue 359.

E.J. Hennink et al., "Evaluation of a Time-Resolved Fluorescence Microscope Using a Phosphorescent Pt-Porphine Model System," Cytometry, 1996, pp. 312-320, Issue 24.

* cited by examiner

BIOCHIP AND APPARATUS FOR DETECTING BIOMATERIAL USING BIOCHIP

CROSS-REFERENCE TO RELATED APPLICATIONS

This U.S. non-provisional patent application claims priority under 35 U.S.C. §119 of Korean Patent Application No. 10-2008-0130958, filed Dec. 22, 2008, the entire contents of which are hereby incorporated by reference.

BACKGROUND OF THE INVENTION

The present invention disclosed herein relates to a biochip and an apparatus for detecting a biomaterial using the biochip, and more particularly, to a biochip capable of enhancing the strength of a fluorescence signal emitted from a fluorophore upon specific binding of the biomaterial, and an apparatus for detecting a biomaterial using the biochip.

An apparatus for detecting a biomaterial (or a biosensor) is used to detect an optical or electrical signal varied with a selective reaction or binding between a biological receptor having the function of recognizing a specific biomaterial and an analyte to be analyzed. That is, the biosensor can confirm the presence of the specific biomaterial, or analyze the specific biomaterial quantitively or qualitively. Here, nucleic acid, protein, cell, tissue, enzyme, antibody and DNA may be used as the biological receptor (e.g., a capture molecule). There are various physical and chemical methods to detect and analyze biomaterials using an electrical signal change according to the presence of the analyte and an optical signal change according to the chemical reaction between the receptor and the analyte.

For an optical biosensor using the change of the optical signal, there is a labeling detection method for detecting a specific antigen quantitively. The labeling detection method uses the change of fluorescence signal strength or radioactive ray generated by a reaction between a labeled antigen and a specific antibody after labeling the specific antibody or antigen with a fluorophore or a radioactive isotope, respectively.

An optical sensor (e.g., fluorescence microscope) for detecting an optical signal from a biomaterial uses fluorescence emitted from a fluorophore to detect and analyze the biomaterial when an incident light having the same wavelength as the absorption wavelength of the fluorophore labeled on antibody or antigen is projected on a sample including the biomaterial. In this case, the fluorophore absorbs a light of a specific wavelength from an external light source, and emits a light of a specific wavelength according to the physical and chemical characteristics.

In the biosensor using the fluorophore, the fluorescence signal is not only emitted from the fluorophore according to the specific reaction of the antigen, but also voluntarily generated from the chip itself, i.e., a plastic material included in the chip. Accordingly, when the fluorescence signal is detected in the analysis of the biomaterial, the voluntary fluorescent signal emitted from the plastic material may act as an obstacle, i.e., a noise.

Also, the fluorescence signal may be generated from the fluorophore not only upon specific reaction between the antigen and the antibody, but also upon nonspecific reaction of the detection antibody labeled with the fluorophore. The fluorescence signal generated from the nonspecific reaction may also act as the noise in the biomaterial analysis.

SUMMARY OF THE INVENTION

The present invention provides a biochip capable of enhancing the strength of an optical signal for a biomaterial analysis.

The present invention also provides an apparatus for detecting a biomaterial, which can enhance the strength of an optical signal for a biomaterial analysis.

Embodiments of the present invention provide biochips including: a metal thin film on the surface of a substrate, restraining autofluorescence of the substrate; and a spacer on the metal thin film, having capture molecules immobilized on the surface of the spacer and specifically bound to target molecules, the spacer having a thickness controlled to enhance the strength of a fluorescence signal emitted from a fluorophore labeled with the target molecules and immobilized on the spacer by the specific binding between the capture molecule and the target molecule.

In other embodiments of the present invention, apparatuses for detecting a biomaterial include: a metal thin film on the surface of a substrate, restraining autofluorescence of the substrate; a spacer on the metal thin film, having capture molecules immobilized on the surface of the spacer and specifically bound to target molecules, the spacer having a thickness controlled to enhance the strength of a fluorescence signal emitted from a fluorophore labeled with the target molecules and immobilized on the spacer by the specific binding between the capture molecule and the target molecule; a light source unit providing an excitation light to the substrate; and a detection unit detecting a fluorescence signal emitted from a fluorophore by the excitation light.

Details of the embodiments will be described in the detail description and the drawings.

BRIEF DESCRIPTION OF THE FIGURES

The accompanying figures are included to provide a further understanding of the present invention, and are incorporated in and constitute a part of this specification. The drawings illustrate exemplary embodiments of the present invention and, together with the description, serve to explain principles of the present invention. In the figures.

DETAILED DESCRIPTION OF PREFERRED EMBODIMENTS

Figure 1:
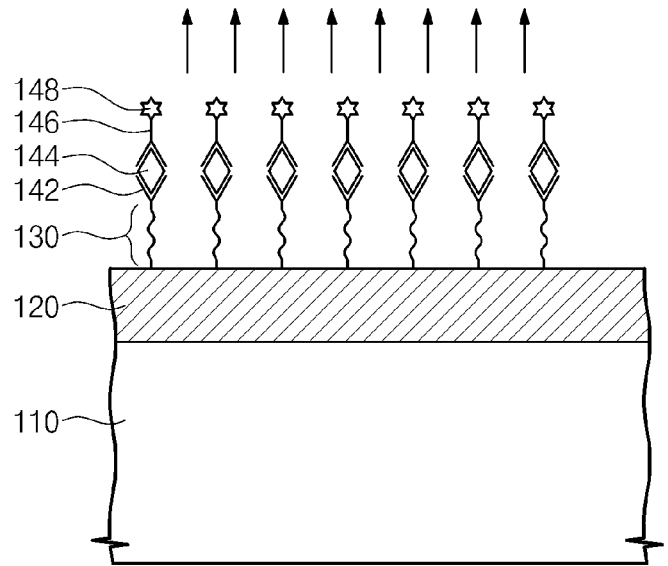
FIG. 1 is a diagram illustrating a biochip according to an embodiment of the present invention.

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Like reference numerals refer to like elements throughout.

As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Additionally, the embodiment in the detailed description will be described with sectional views as ideal exemplary views of the present invention. Accordingly, shapes of the exemplary views may be modified according to manufacturing techniques and/or allowable errors. Therefore, the embodiments of the present invention are not limited to the specific shape illustrated in the exemplary views, but may include other shapes that may be created according to manufacturing processes. Areas exemplified in the drawings have general properties, and are used to illustrate a specific shape of a device region. Thus, this should not be construed as limiting the scope of the present invention.

Target molecules set forth herein, which are biomolecules representing a specific matrix, may be construed as the same meaning as analyte, and corresponds to antigen in embodiments of the present invention.

Capture molecules set forth herein, which are biomolecules specifically bound to the target molecules, may be construed as the same meaning as probe molecules, receptors or acceptors, and correspond to capture antibody in embodiments of the present invention. Also, a sandwich immunoassay is used to detect a biomaterial in embodiments of the present invention. Furthermore, detection molecules may be biomolecules capable of being specifically bound to the target molecules by being labeled with a fluorophore, and media capable of attaching the fluorophore to the target molecules.

Hereinafter, exemplary embodiments of the present invention will be described in detail with reference to the accompanying drawings.

FIG. 1 is a diagram illustrating a biochip according to an embodiment of the present invention. A biochip according to an embodiment of the present invention may be applied to a DNA chip, a protein chip, a micro array, or a micro fluid chip.

Referring to FIG. 1, a biochip 10 according to an embodiment of the present invention includes a substrate 110, a metal thin film 120, a spacer 130, and a capture molecule 142 fixed on the surface of the spacer 130.

The substrate 110 may be formed of a material transmitting and reflecting a light. For example, the substrate 110 may be plastic, glass, or silicon substrate. Also, the substrate 110 may be formed of a polymer such as PDMS (polydimethylsiloxane), PMMA (polymethylmethacrylate), PC (polycarbonate), COC (cyclic olefin copolymer), PA (polyamide), PE (polyethylene), PP (polypropylene), PPE (polyphenylene ether), PS (polystyrene), POM (polyoxymethylene), PEEK (polyetheretherketone), PTFE (polytetrafluoroethylene), PVC (polyvinylchloride), PVDF (polyvinylidene fluoride), PBT (polybutyleneterephthalate), FEP (fluorinated ethylenepropylene), and PFA (perfluoroalkoxyalkane).

The substrate 110 may have autofluorescence characteristic, and a fluorescence noise emitted from the substrate 110 itself may have an effect on a detection of a fluorescence signal emitted from the fluorophore 148 when a target molecule 144 is specifically bound to the capture molecule 142.

Figure 2:
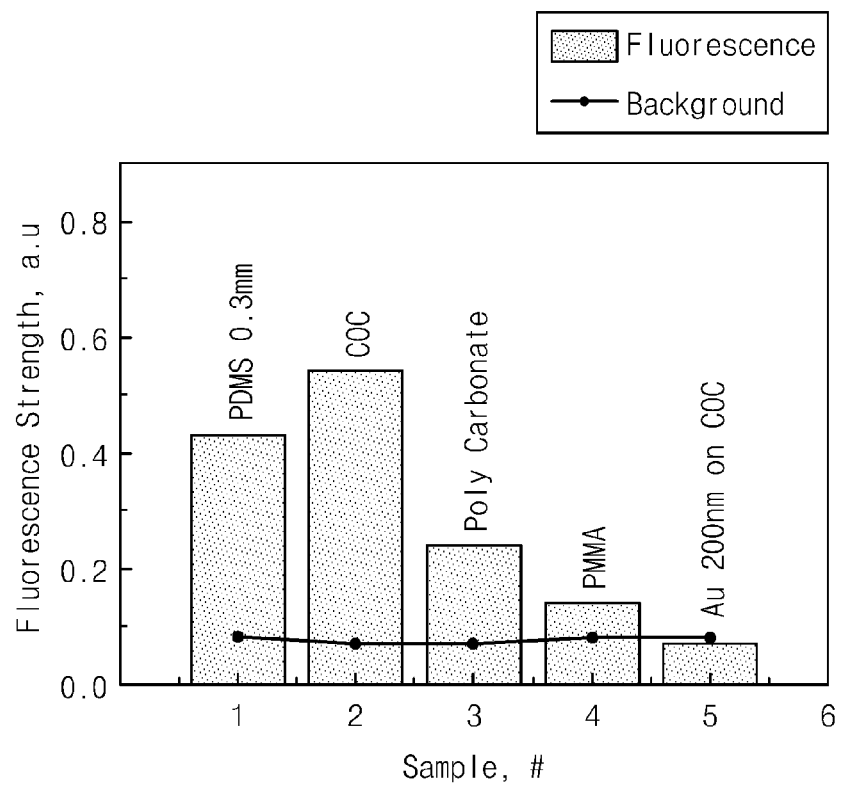
FIG. 2 is a graph illustrating a comparison between autofluorescence of plastic substrates used in a typical biochip and autofluorescence of substrates used in a biochip according to embodiments of the present invention.

The metal thin film 120 may be formed on the surface of the substrate 110, and restrain the autofluorescence characteristic of the substrate 110. Specifically, the metal thin film 120 may serve as a reflecting mirror upon signal detection for an analysis of a target molecule 144. For example, the metal thin film 120 may be formed of Au, Ag, Cr, Ni, Al or Ti, and may have a thickness of about 50 nm to about 300 nm. A restraint effect on the autofluorescence characteristic of a plastic substrate in a biochip according to an embodiment of the present invention is illustrated in FIG. 2.

Also, an adhesive thin film (not shown) may be formed on the interface between the substrate 110 and the metal thin film 120 to enhance the adhesive strength of the metal thin film 120. The adhesive thin film (not shown) may include, e.g., a Cr thin film or a Ti thin film, and may be formed in a thickness of about 1 nm to about 20 nm.

The spacer 130 may be formed on the surface of the metal thin film 120, and control the optical path length between the metal thin film 120 and the fluorophore 148 connected to the spacer 130. That is, the optical path length between the metal thin film 120 and the fluorophore 148 may be varied with the thickness of the spacer 130. The optical distance between the metal thin film 120 and the fluorophore 148 changes the strength of the fluorescence signal emitted from the fluorophore 148. The thickness of the spacer 120 may be varied according to the luminescence center wavelength of the fluorophore 148. That is, the optical path length between the fluorophore 148 and the metal thin film 120 may be selected according to the luminescence center wavelength of the fluorophore 148 to enhance the strength of the fluorescence signal emitted from the fluorophore 148. Detail description thereof will be described in detail with reference to FIGS. 4 and 5.

The spacer 130 may be formed of an organic material, an oxide, a nitride, or an inorganic material, more specifically, $SiO_2$, $Si_3N_4$, $TiO_2$, or $Al_2O_3$.

The surface of the spacer 130 may be processed in order to immobilize the capture molecule 142. For example, a polymer including poly lysine may be formed on the surface of the spacer 130, and a self assembled monolayer may be formed. In order to immobilize the capture molecule 142 on the surface of the spacer 130, an active group may be induced on the surface of the spacer 130. For example, active groups such as carboxyl (—COOH), thiol (—SH), hydroxyl (—OH), silane, amine, and epoxy may be induced on the surface of the spacer 130.

The capture molecules 142, which are materials specifically reacting or binding with the target molecules 144 to be analyzed, are immobilized on the surface of the spacer 130. As a method for immobilizing the capture molecules 142 on the surface of the spacer 130, a chemical absorption, a covalent-binding, an electrostatic attraction, a co-polymerization, or an avidin-biotin affinity system may be used.

The capture molecules 142 may be, e.g., protein, cell, virus, nucleic acid, organic molecule, or inorganic molecule. In case of the protein, the capture molecules 142 may be any biomaterial such as an antigen, an antibody, a matrix protein, an enzyme, and a co-enzyme. In case of the nucleic acid, the capture molecules 142 may be DNA, RNA, PNA, LNA, or a hybrid thereof. More specifically, the capture molecules 142 according to an embodiment of the present invention may be capture antibodies capable of specifically binding with antigens.

On the other hand, the target molecules 144, i.e., antigens provided from the outside are specifically bound to the captured molecules 142. In this case, the target molecules 144 are labeled by the fluorophore 148, and specifically bound to the capture molecules 142. More specifically, a detection molecule 146 is specifically bound to the target molecule 144, so that the target molecule can be labeled with the fluorophore 148. In this case, the detection molecules 146 and the capture molecules 142 are specifically bound to each other at a different site. The detection molecules 146 according to an embodiment of the present invention may be a detection antibody capable of specifically binding with an antigen.

Thus, the target molecules 144 labeled with the fluorophore 148 are specifically bound to the capture molecules 142, so that a structure of the capture molecule 142—target molecule 144—detection molecule 146—fluorophore 148 can be formed on the surface of the spacer 130. Accordingly, a monolayer including the fluorophores 148 can be formed on the upper part of the spacer 130.

Thus, the fluorophores 148 connected to the upper part of the spacer 130 allows an absorption and emission of a light at their surface when the excitation light is provided from the outside. The fluorophores 148 have the characteristic that a light emitted from the surface is extinguished if a predetermined time is lapsed after the excitation light is projected on the surface. Detail description thereof will be described with reference to FIG. 9.

The wavelength and strength of a light (i.e., a fluorescent signal) emitted from the fluorophore 148 vary with the type of the fluorophore and peripheral materials. That is, the wavelength and strength of the light emitted from the fluorophore 148 may vary with the specific reaction between the target molecule 144 and the capture molecule 142.

An interference phenomenon may occur between the light emitted from the fluorophore 148 and a light reflected from a metal thin film 120 under the spacer 130. Accordingly, the light emitted from the fluorophore 148, i.e., the strength of the fluorescence signal, the angular distribution, and the decay time may be varied.

FIG. 2 is a graph illustrating autofluorescence characteristic of a plastic material used in a typical biochip, and autofluorescence characteristic of substrate having a metal thin film thereon in a biochip according to an embodiment of the present invention. That is, FIG. 2 illustrates the strength of the fluorescence signal according to the type of the biochip substrate.

In FIG. 2, the samples #1 through #4 are plastic materials used in a typical biochip, and the sample #5 represents a plastic substrate having a metal thin film thereon according to an embodiment of the present invention.

Referring to FIG. 2, it will be understood that the plastic materials used as a substrate have the autofluorescence characteristic. A COC substrate may have higher autofluorescence characteristic than other plastic substrates. However, if an Au thin film having a thickness of about 200 nm is formed on the COC substrate, the autofluorescence characteristic may be significantly reduced. Therefore, it will be understood that a metal thin film formed on the surface of the plastic substrate may restrain the voluntarily generated fluorescence characteristics in the plastic substrate.

Figure 3:
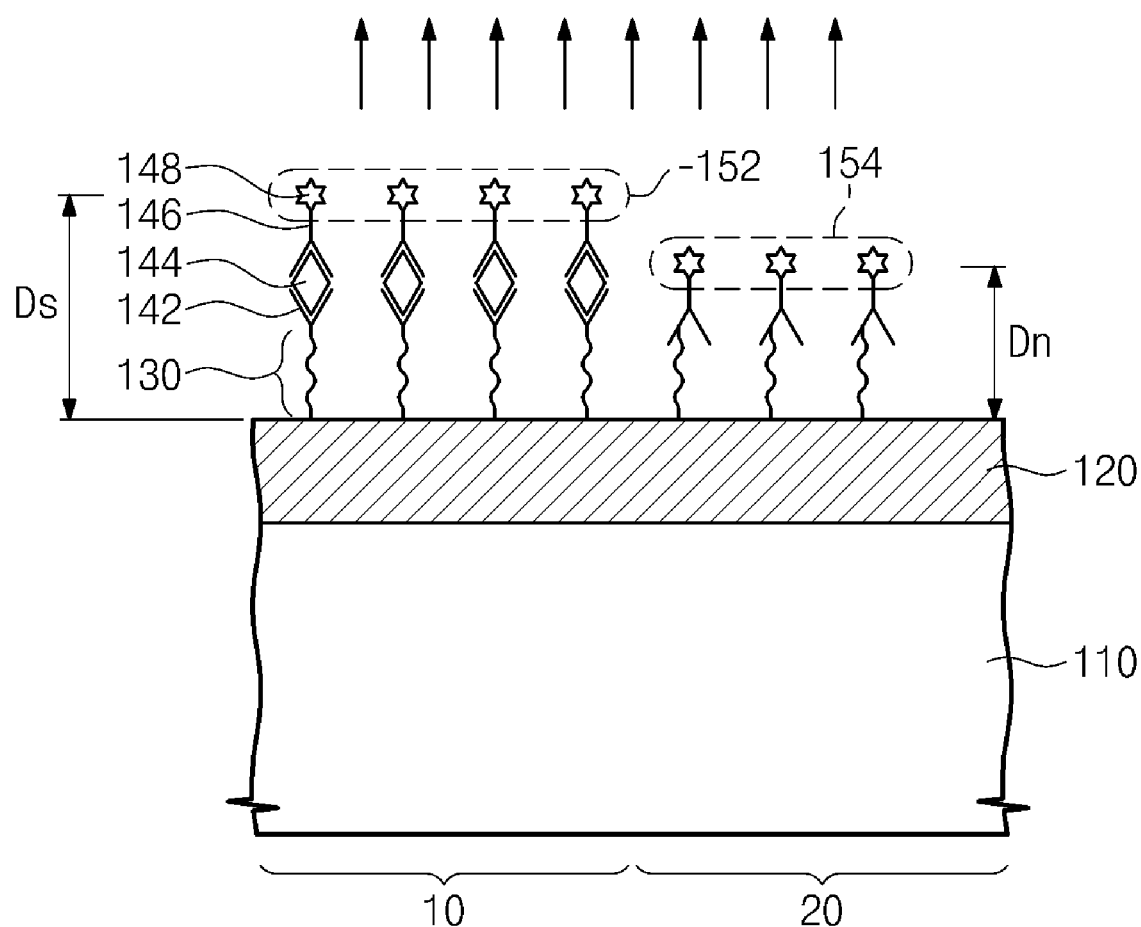
FIG. 3 is a diagram illustrating a specific binding region and a nonspecific region in a biochip according to an embodiment of the present invention.

FIG. 3 is a diagram illustrating a specific binding region between a capture molecule and a target molecule and a nonspecific region in a biochip according to an embodiment of the present invention.

Referring to FIG. 3, the biochip may include a specific binding region in which a capture molecule 142 is specific bound to a target molecule 144, and a nonspecific binding region. The specific binding region 10 has a binding structure of the capture molecule 142—target molecule 144—detection molecule 146—fluorophore 148 on a spacer 130. In the nonspecific binding region 20, the detection molecules 146 labeled with the fluorophore 148 may be directly bound to the surface of the spacer 130 or the top surface of the metal thin film 120 because the target molecules 144 are non-specifically bound to the capture molecules 142 and the detection molecules 146.

Accordingly, a first fluorophore layer 152 formed by the specific reaction between the capture molecule 142 and the target molecule 144, and a second fluorophore layer 154 formed by the nonspecific reaction of the detection molecule 146 labeled with the fluorophore 148 may be formed on the spacer 130. In the nonspecific binding region 20, an optical path length $D_n$ between the second fluorophore layer 154 and the metal thin film 120 is smaller than an optical path length $D_s$ between the first fluorophore layer 152 and the metal thin film 120.

Thus, the optical path length difference between the fluorophore and the metal thin film 120 may cause a change of the strength of the fluorescence signal emitted from the fluorophore 148. Detail description thereof will be more fully described with reference to FIG. 4.

Figure 4:
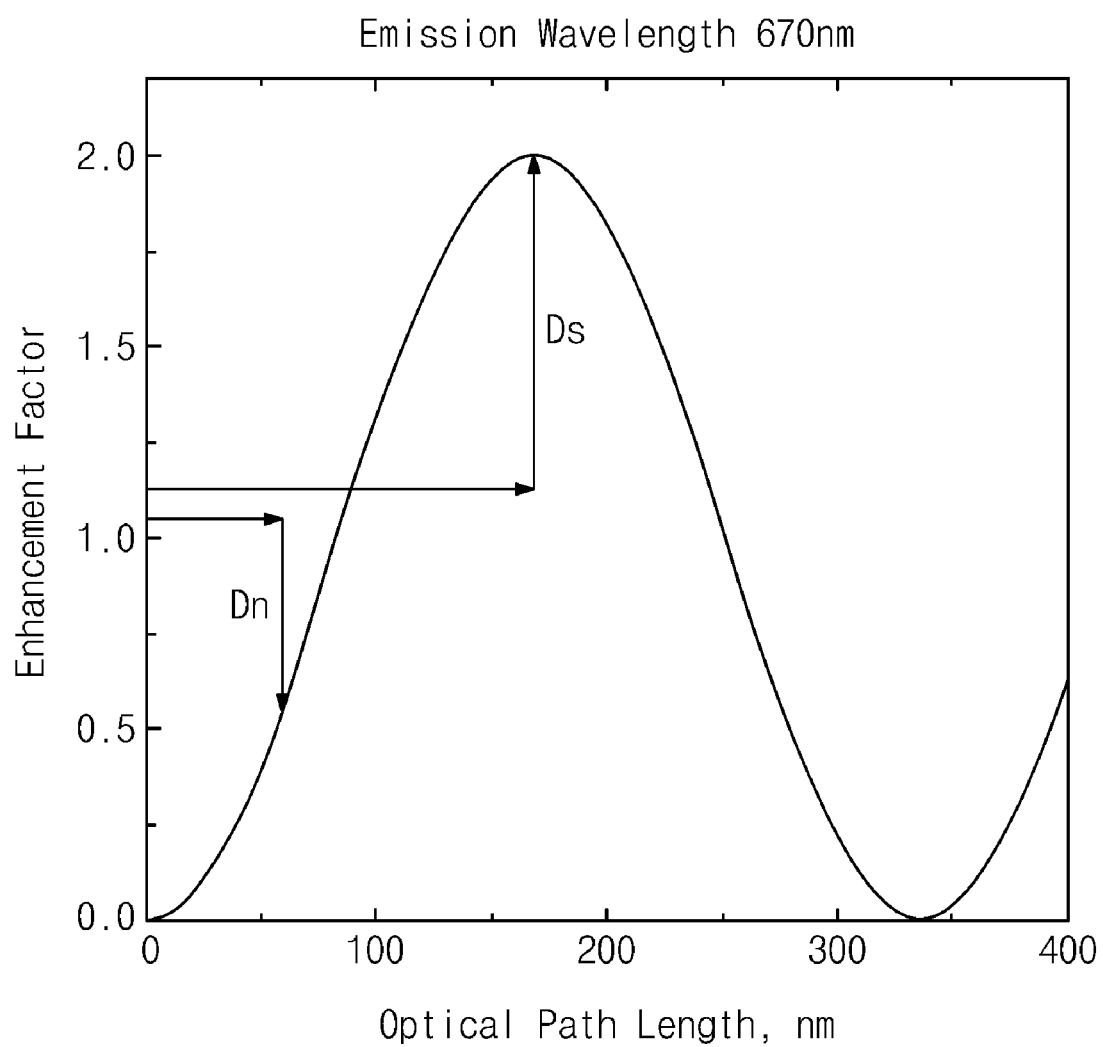
FIG. 4 is a graph illustrating the change of a fluorescence signal enhancement factor according to an optical path length between a fluorophore and a metal thin film in a chip according to an embodiment of the present invention.

FIG. 4 is a graph illustrating a change of a fluorescence signal enhancement factor according to an optical path length between a fluorophore and a metal thin film in a chip according to an embodiment of the present invention.

Referring to FIG. 4, it will be understood that, when the wavelength of a light emitted from the fluorophore is about 670 nm, the fluorescence signal enhancement factor, i.e., the strength of the fluorescence signal varies with the optical path length between the fluorophore and the metal thin film. Also, it will be understood that the fluorescence strength of the fluorophore is enhanced or restrained according to the optical path length.

That is, when the optical path length is from about 100 nm to about 250 nm, the enhancement factor becomes more than 1, thereby enhancing the strength of the fluorescence signal emitted from the fluorophore. In addition, it will be understood that, when the optical path length is from about 160 nm to about 170 nm, a light reflected from the metal thin film causes a constructive interference.

Accordingly, when a fluorophore having an emission wavelength of about 670 nm is used in the biochip in FIG. 3, the thickness of the spacer 130 may be controlled so that the optical path length between the metal thin film 120 and the fluorophore 148 immobilized due to the specific binding between the capture molecule 142, the target molecule 144, and the detection molecule 146 may be from about 100 nm to about 250 nm.

Moreover, since the thickness of the spacer 130 is controlled so that the strength of the fluorescence signal emitted from the fluorophore 148 may be maximized when the capture molecule 142, the target molecule 144, and the detection molecule 146 are specifically bound to each other, the strength of the fluorescence signal emitted from the second fluorophore layer 154 can be restrained. That is, when the optical path length $D_s$ between the first fluorophore layer 152 and the metal thin film 120 is optimized, the strength of the fluorescence signal emitted from the optical path length $D_n$ between the second fluorophore layer 154 and the metal thin film 120 is weakened.

Referring again to FIGS. 3 and 4, in the optical path length between the first fluorophore layer 152 and the metal thin film 120, the thickness of the spacer 130 is controlled so that the strength of the fluorescence signal emitted from the first fluorophore 152 may be maximized. In the optical path length $D_n$ between the second fluorophore layer 154 and the metal thin film 120, the strength of the fluorescence signal emitted from the second fluorophore layer 154 can be restrained.

Therefore, by controlling the thickness of the spacer 130 so as to cause the constructive interference between the fluorescence signal emitted from the fluorophore 148 and the light reflected from the metal thin film 120, the strength of the fluorescence signal emitted from the fluorophore 148 can be enhanced due to the specific binding of the target molecule 144, while the strength of fluorescence signal can be restrained due to the nonspecific binding of the detection molecule 146.

Figure 5:
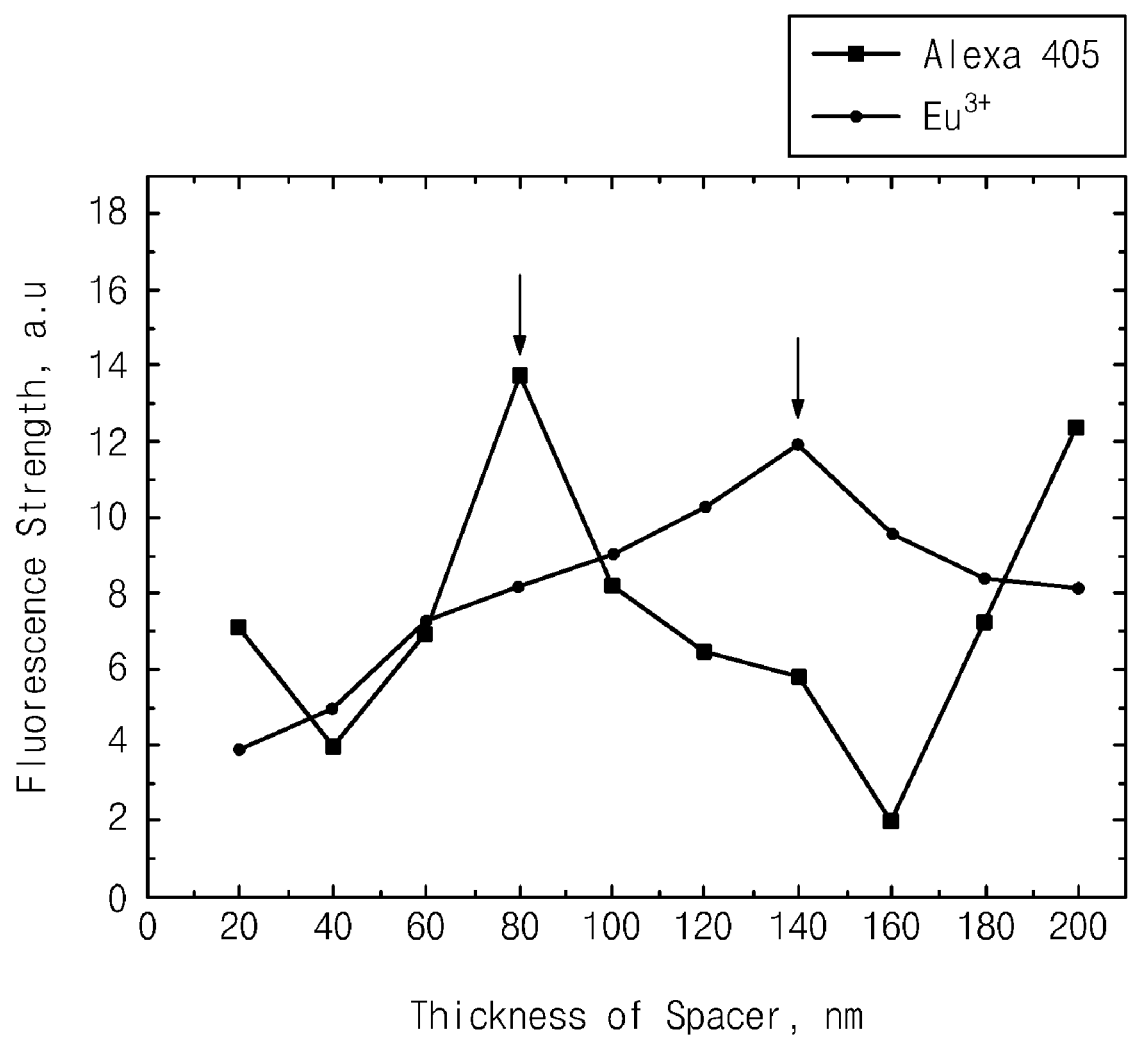
FIG. 5 is a graph illustrating the change of fluorescence signal strength according to the thickness of a spacer in a biochip according to an embodiment of the present invention.

FIG. 5 is a graph illustrating a change of the fluorescence signal strength according to the thickness of a spacer in a biochip according to an embodiment of the present invention.

Referring to FIG. 5, the fluorescence signal strength of Alexa Fluor® 405 and $Eu^{3+}$ is varied according to the thickness of the spacer. That is, it is shown that the thickness of the spacer for the maximum fluorescence signal strength of the fluorophore is different from each other. The Alexa Fluor® 405 represents the maximum fluorescence signal strength when the thickness of the spacer is from about 70 nm to about 90 nm. The $Eu^{3+}$ represents the maximum fluorescence signal strength when the thickness of the spacer is from about 130 nm to about 150 nm. Accordingly, in the biochip according to embodiments of the present invention, the thickness of the spacer may be varied according to the type of the fluorophores and the luminescence center wavelength thereof.

That is, in a biochip for a biomaterial analysis according to embodiments of the present invention, the thickness of the spacer for the Alexa Fluor® 405 is controlled to be from about 70 nm to about 90 nm so as to represent the maximum fluorescence signal strength, and the thickness of the spacer for the $Eu^{3+}$ is controlled to be from about 130 nm to about 150 nm so as to represent the maximum fluorescence signal strength.

Figure 6:
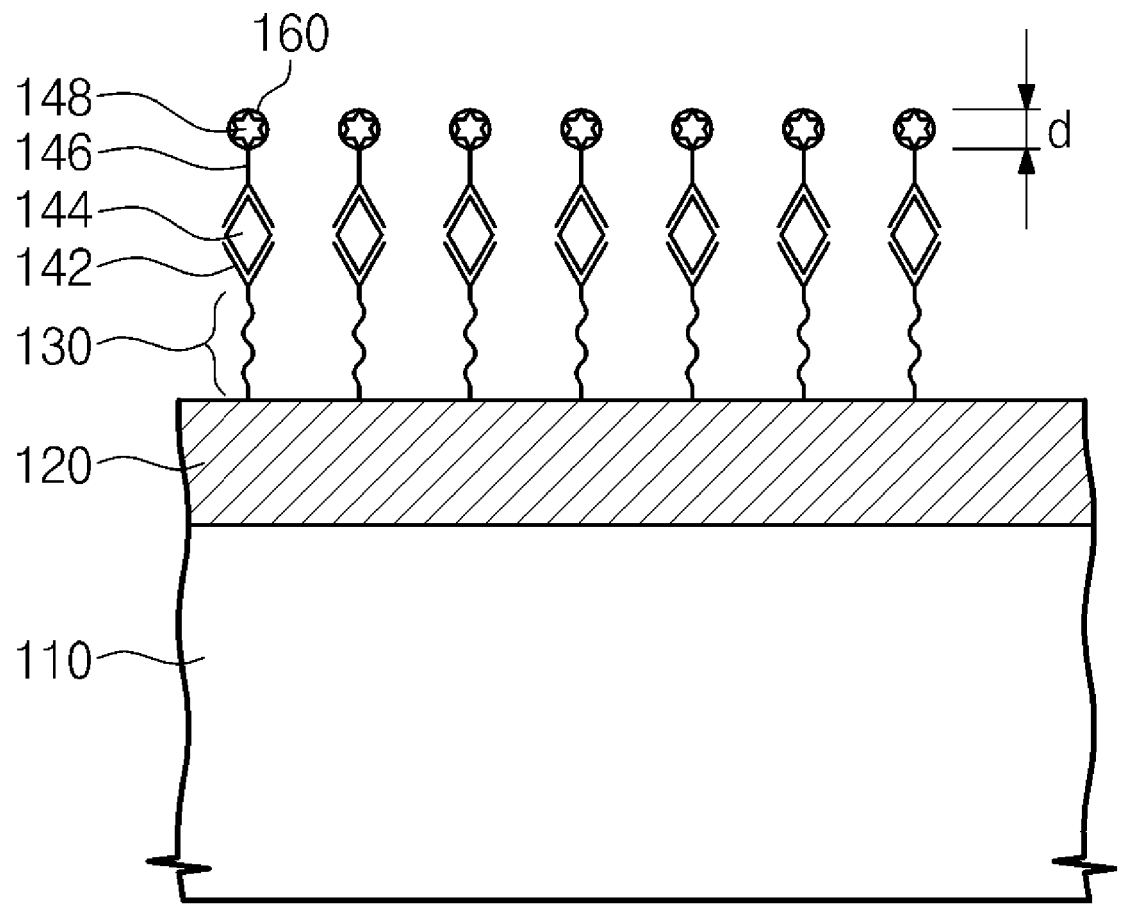
FIG. 6 is a diagram illustrating a biochip using a fluorophore bead according to an embodiment of the present invention.

FIG. 6 is a diagram illustrating a biochip having a fluorophore having a valid size fixed thereon according to an embodiment of the present invention.

Referring to FIG. 6, the fluorophores labeled on a detection molecule 146 may have a bead type including fluorophore particles 148. That is, the fluorophore beads 160 may be fixed on the upper part of a spacer 130.

Target molecules 144 may be specifically bound to the detection molecules 146 labeled with the fluorophore beads 160. The fluorophore bead 160, which is a structure containing a plurality of fluorophore particles in a polymer bead, may have a predetermined size. Accordingly, in the biochip according to the embodiment of the present invention, a binding structure of the capture molecule 142—target molecule 144—detection molecule 146—fluorophore bead 160 may be formed on the spacer 130.

By labeling the target molecules 144 with the fluorophore bead 160, the strength of the fluorescence signal emitted from the fluorophore can be enhanced because the amount of the fluorophore immobilized on the spacer 130 increases when the capture molecule 142 is specifically bound to the target molecules 144.

The fluorophore bead 160 may have a valid size of a diameter d. Also, the maximum value of the enhancement factor in the strength of the fluorescence signal emitted from the fluorophore may vary according to the valid size of the fluorophore bead 160. Detail description thereof will be described with respect to FIG. 7.

Figure 7:
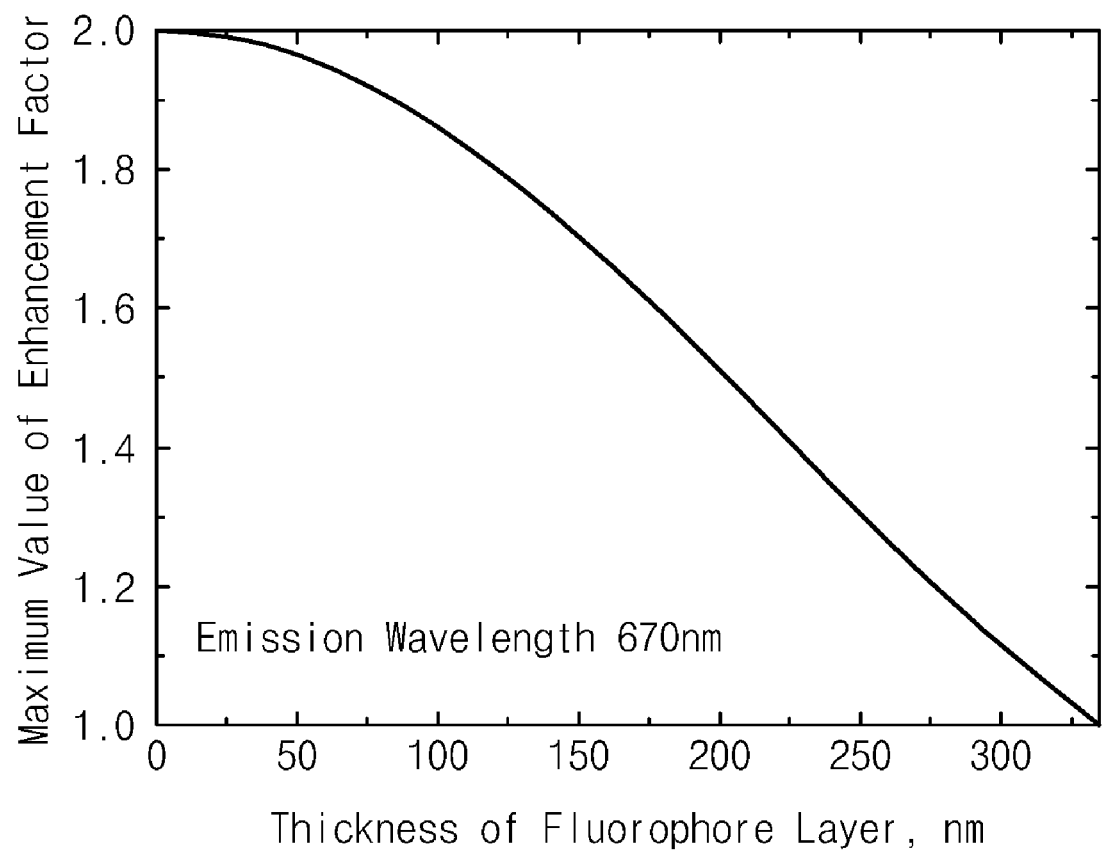
FIG. 7 is a graph illustrating the change of the maximum value of an enhancement factor according to the size of a fluorophore bead in a biochip.

FIG. 7 is a graph illustrating a change of the maximum value of an enhancement factor of a fluorescence signal according to a valid size of a fluorophore in an embodiment of the present invention.

Referring to FIG. 7, when the valid size of the fluorophore is more than a predetermined value, the maximum value of the enhancement factor becomes 1, thereby causing the fluorescence signal to be impossible to enhance. Accordingly, in order to enhance to fluorescence signal emitted according to the specific reaction, the thickness of the spacer must be controlled while the fluorophore having a valid size less than a predetermined value is used.

That is, in a biochip according to an embodiment of the present invention, the thickness of the space may be minutely controlled in order to maximize the fluorescence signal according to the luminescence center wavelength of the fluorophore and the valid size of the fluorophore bead immobilized on the spacer due to the specific binding between the target molecule and the capture molecule.

Hereinafter, a biomaterial detection apparatus according to an embodiment of the present invention will be described in detail with reference to FIG. 8.

Figure 8:
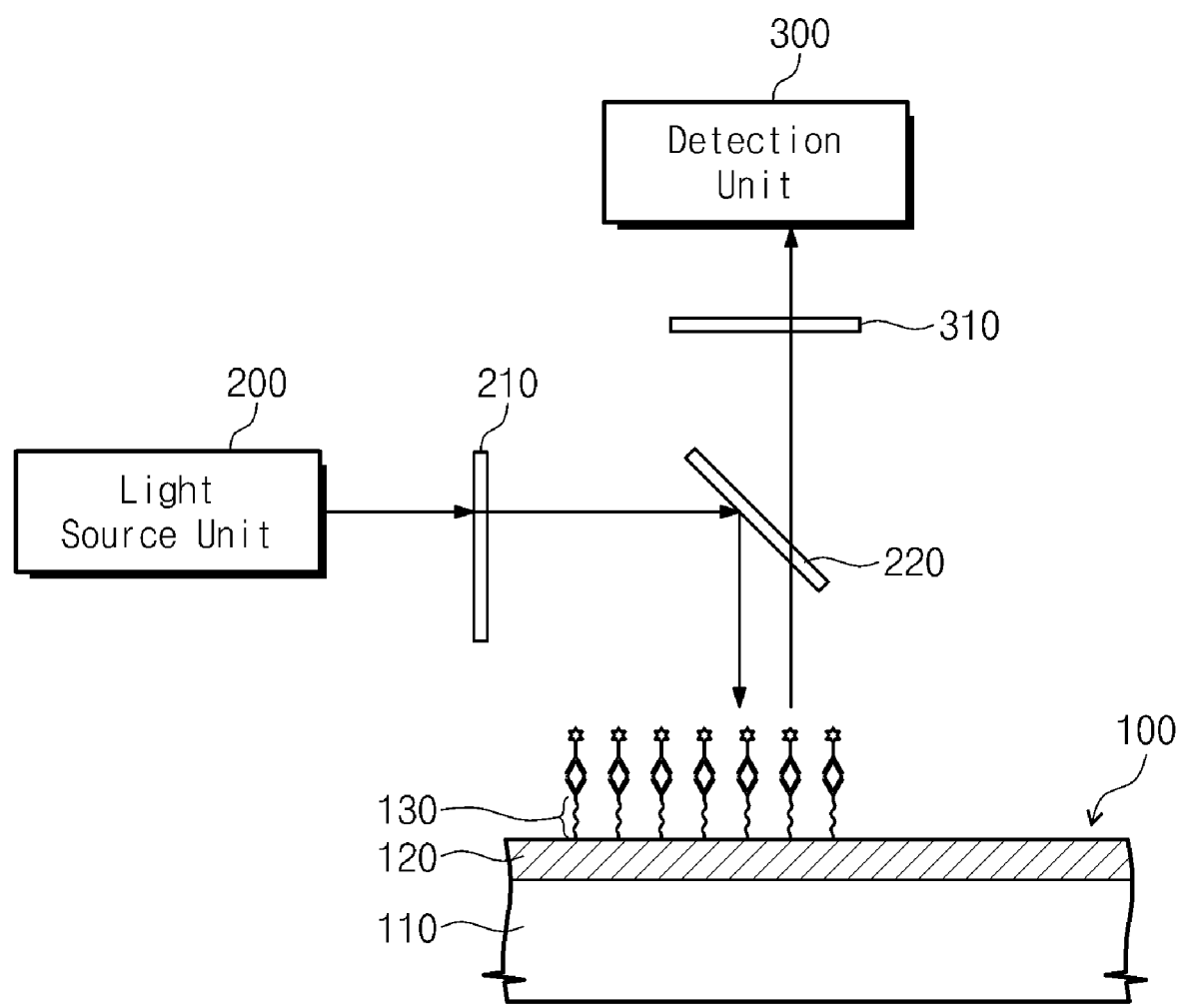
FIG. 8 is a diagram illustrating the configuration of a biomaterial detection apparatus according to an embodiment of the present invention.

FIG. 8 is a diagram illustrating a configuration of a biomaterial detection apparatus according to an embodiment of the present invention.

Referring to FIG. 8, the biomaterial detection apparatus includes a biochip 100, a light source unit 200, and a detection unit 300.

The biochip 100, as described in FIG. 1, includes a substrate 110, a metal thin film 129, a spacer 130, and capture molecules 142 immobilized on the surface of the spacer 130. Target molecules 144 to be analyzed are labeled with fluorophore 148 in the biochip 100. The target molecules 144 provided in the biochip 100 are specifically bound to the capture molecules 142. Accordingly, the fluorophores 148 may be immobilized on the upper part of the spacer 130.

In this case, the thickness of the spacer 130 is controlled such that the strength of the fluorescence signal emitted from the fluorophore 148 may be enhanced when the target molecule 144 is specifically reacted with the capture molecule 142 and the detection molecule 146, and such that the strength of the fluorescence signal may be weaken when the detection molecule is nonspecifically reacted. That is, according to an embodiment of the present invention, when the Alexa Fluor® 405 having a luminescence wavelength of about 430 nm is used as the fluorophore 148, the thickness of the spacer 130 may be from about 70 nm to about 90 nm. Also, according to another embodiment of the present invention, when the Eu3+ having a luminescence wavelength of about 615 nm is used as the fluorophore 148, the thickness of the spacer 130 may be from about 120 nm to about 160 nm.

The light source unit 200 provides an excitation light having a specific wavelength to the biochip 100 according to the absorption wavelength characteristics of the fluorophore 148 used in a biomaterial analysis. The excitation light projected from the light source unit 200 may be provided in a pulse form in consideration of the luminescence lifetime of the fluorophore 148.

The light source unit 200 may include a Xenon lamp outputting the polychromatic light. If the Xenon lamp is used, the light source unit 200 may include an optical filter to provide a monochromatic light as an excitation light.

Also, in order to provide an excitation light of a pulse form to the biochip 100, a pulse laser may be used as the light source unit 200. By installing an optical chopper 210 at an incident path of the excitation light, an excitation light having a pulse form may be continuously provided to the biochip 100. In this case, the optical chopper 210, which is a rotatable disk with a slit, blocks or passes the excitation light projected from the light source unit 200. Also, a mirror 220 may be installed to reflect the excitation light from the light source unit 200 to the biochip 100.

The detection unit 300 detects a fluorescence signal emitted from the fluorophore 148 in the biochip 100. That is, if a short pulse of excitation light from the light source unit 200 is projected to the fluorophore 148 in the biochip 100, a fluorescence signal is emitted from the fluorophore 148. The emission of the fluorescence signal from the fluorophore 148 lasts for a determined period according to the luminescence lifetime of the fluorophore 148.

On the other hand, when the emission light from the fluorophore 148 is detected by the detection unit 300, in order to restrain the detection of the pulse of the excitation light, it is desirable that the emission time of the emission light from the fluorophore 148 should be longer than the time taken for the pulse of the excitation light to be provided. Accordingly, fluorophores having a luminescence lifetime of more than 1 μs can be used. The fluorophores having the luminescence lifetime of more than 1 μs may include, e.g., a Europium ($Eu^{3+}$), a platinum, a strontium aluminate, and a zinc sulfide. That is, when the luminescence lifetime of the fluorophore is long, the excitation light pulse may have a different peak time from the emission light pulse. Accordingly, when the emission light is detected by the detection unit 300, the detection of the excitation light and a fluorescence signal emitted during a short period can be restrained. Detail description thereof will be described with reference to FIGS. 9 and 10.

Additionally, an optical filter 310 may be provided to detect only an emission light emitted from the fluorophore 148. The emission light emitted from the fluorophore 148 enters the detection unit 300 through the optical filter 310.

Figure 9:
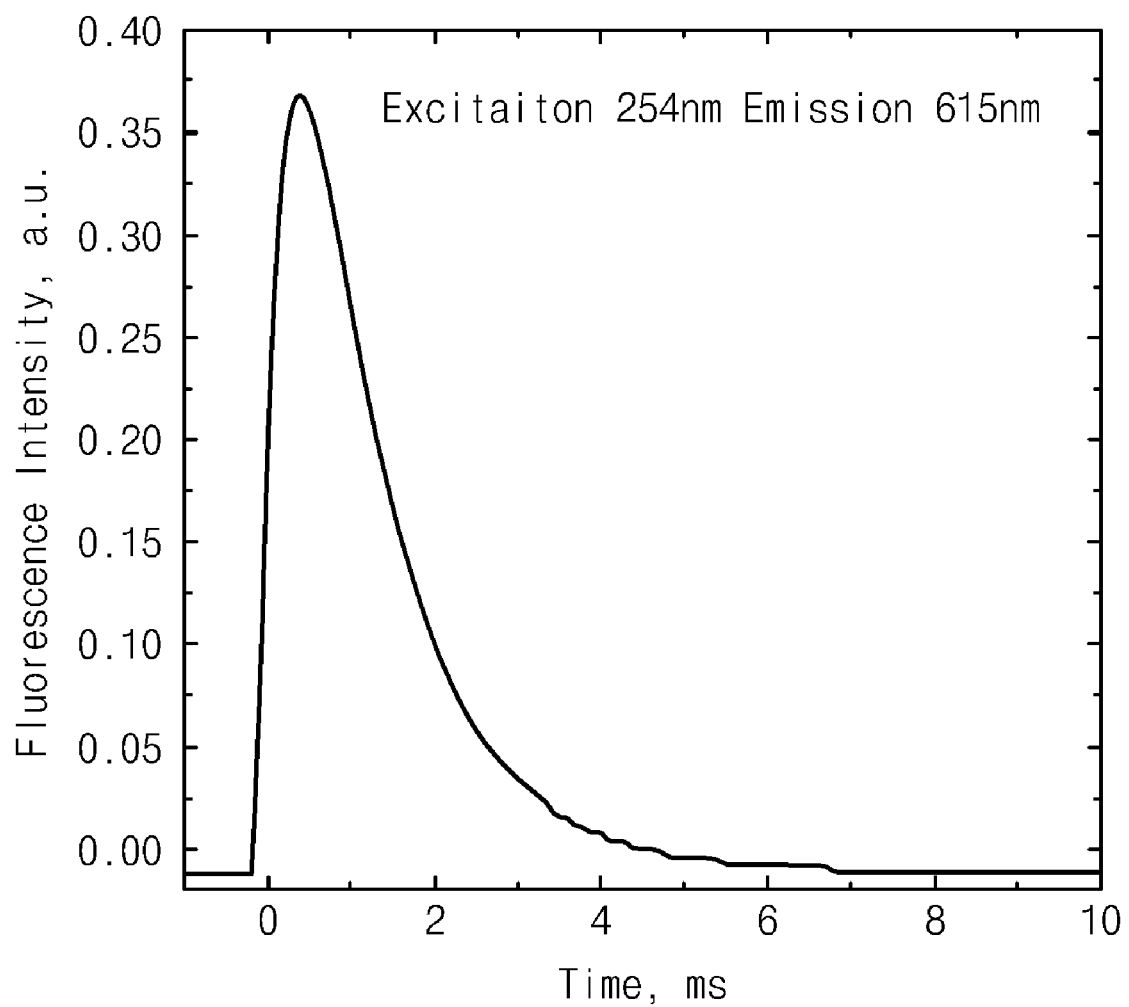
FIG. 9 is a graph illustrating the change of fluorescence signal strength with time, when Europium ($Eu^{3+}$) is used as a fluorophore, in a biochip according to an embodiment of the present invention.

FIG. 9 is a graph illustrating the change of fluorescence signal strength with time, when Europium ($Eu^{3+}$) is used as a fluorophore, in a biochip according to an embodiment of the present invention.

Referring to FIG. 9, after a short pulse (pulse time width is 1 μs) of excitation light having a wavelength of about 405 nm (or about 254 nm) was projected on the $Eu^{3+}$, the strength change of the fluorescence signal emitted from the $Eu^{3+}$ was detected with the passage of time. The $Eu^{3+}$ emitted the fluorescence signal during a relatively long period. The fluorescence signal was rapidly extinguished after about 2 ms. That is, it was shown that the $Eu^{3+}$ has a luminescence lifetime of about 2 ms.

Figure 10:
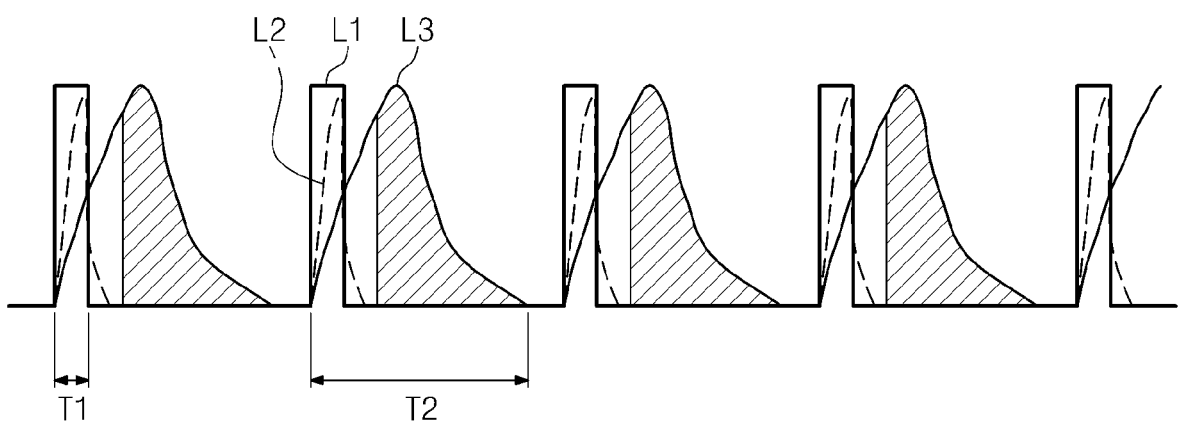
FIG. 10 is a timing diagram illustrating an excitation light and an emission light in a biomaterial detection apparatus according to an embodiment of the present invention.

FIG. 10 is a timing diagram illustrating an excitation light and an emission light when a fluorophore having a long luminescence lifetime is used in a biochip according to an embodiment of the present invention.

Referring to FIG. 10, when an excitation light pulse L1 having a pulse width T1 of about 1 μs is provided while using a fluorophore having a long luminescence time T2 of about 2 ms, an emission light pulse L3 different from the excitation light pulse L1 may be detected. That is, the emission light emitted from the fluorophore is detected during a cycle of the excitation light pulse L1. If the emission light is detected at a peak time of the emission light strength, the excitation light pulse L1 and the emission light pulse L2 of the fluorophore having a short luminescence lifetime are extinguished so that only the emission light L3 can be detected.

That is, when a fluorescent signal is detected at the peak time of the emission light strength, signal-to-noise ratio can be enhanced. Accordingly, when the target molecule specifically reacts with the capture molecule, the detection efficiency of the fluorescence signal emitted from the fluorophore can be improved.

According to the embodiments of the present invention, the metal thin film formed on the substrate in the biochip and the apparatus for detecting biomaterials can restrain the fluorescence signal self-emitted from the substrate.

Also, the spacer on the metal thin film, having a thickness controlled according to the luminescence center wavelength of the fluorophore used in the biomaterial analysis, can enhance the strength of the fluorescence signal emitted from the fluorophore upon specific reaction of the biomaterial.

Furthermore, the detection efficiency of the fluorescence signal detected by the specific reaction of the biomaterial can be improved by restraining the fluorescence signal detected by the nonspecific reaction of the biomaterial using the strength change of the fluorescence signal of the fluorophore according to the optical path length.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A biochip comprising:
    a metal thin film on the surface of a substrate, configured to restrain autofluorescence of the substrate;
    a spacer disposed over the thin metal film and having a predetermined thickness;
    a plurality of capture molecules immobilized on the surface of the spacer;
    a first portion of the plurality of capture molecules that are specifically bound to target molecules;
    a second portion of the plurality of capture molecules that are non-specifically bound to fluorescent detection molecules;
    a first fluorophore layer comprising a plurality of fluorescent detection molecules coupled, by binding to the target molecule that are specifically bound, to the first portion of the plurality of capture molecules; and
    a second fluorophore layer comprising a plurality of fluorescent detection molecules non-specifically bound to the second portion of the plurality of capture molecules;
    wherein the predetermined thickness is of a thickness determined to cause constructive interference between light directly emitted from the first fluorophore layer and light emitted from the first fluorophore layer and reflected by the metal thin film, and to restrain light emitted from the second fluorophore layer.

2. The biochip of claim 1, wherein the substrate is formed of any selected from the group consisting of polydimethylsiloxane (PDMS), polymethylmethacrylate (PMMA), polycarbonate (PC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), and perfluoralkoxyalkane (PFA).

3. The biochip of claim 1, wherein the metal thin film is formed of any selected from the group consisting of Ag, Cr, Ni, Al, and Ti.

4. The biochip of claim 1, wherein the spacer is formed of any selected from the group consisting of an oxide, a nitride, and an inorganic material.

5. The biochip of claim 1, wherein the spacer further comprises a polymer selected from the group consisting of a poly lysine and a self-assembled molecular monolayer (SAM).

6. The biochip of claim 1, wherein the capture molecules are immobilized by any selected from the group consisting of thiol (—SH), hydroxyl (—OH), silane, amine and epoxy, which are induced on the surface of the spacer.

7. The biochip of claim 1, wherein the fluorophores of the first and second fluorophore layers have a beaded shape comprising a plurality of fluorescent particles.

8. The biochip of claim 1, wherein the fluorophore is selected from the group consisting of a platinum, a strontium aluminate, and a zinc sulfide.

9. An apparatus for detecting a biomaterial, the apparatus comprising:
  a metal thin film on the surface of a substrate, restraining autofluorescence of the substrate;
  a spacer disposed over the thin metal film and having a predetermined thickness;
  a plurality of capture molecules immobilized on the surface of the spacer;
  a first portion of the plurality of capture molecules that are specifically bound to target molecules;
  a second portion of the plurality of capture molecules that are non-specifically bound to fluorescent detection molecules;
  a first fluorophore layer comprising a plurality of fluorescent detection molecules coupled, by binding to the target molecule that are specifically bound to the first portion of the plurality of capture molecules;
  a second fluorophore layer comprising a plurality of fluorescent detection molecules non-specifically bound the second portion of the plurality of capture molecules;
  a light source unit configured to provide an excitation light to the substrate; and
  a detection unit configured to detect a fluorescence signal emitted from a fluorophore by the excitation light;
  wherein the predetermined thickness is of a thickness determined to cause constructive interference between light directly emitted from the first fluorophore layer and light emitted from the first fluorophore layer and reflected by the metal thin film, and to restrain light emitted from the second fluorophore layer.

10. The apparatus for detecting a biomaterial of claim 9, wherein the fluorescence signal emitted from the fluorophore is excited by the excitation light and enhanced by a light reflected from the metal thin layer.

11. The apparatus for detecting a biomaterial of claim 9, wherein the light source unit emits the excitation light in a pulse form.

12. The apparatus for detecting a biomaterial of claim 11, wherein the fluorophore has a longer fluorescence lifetime than the pulse width of the excitation light.

13. The apparatus for detecting a biomaterial of claim 9, wherein the detection unit detects the fluorescent signal emitted from the fluorophore through a time-resolved fluorescence measurement method.

14. The apparatus for detecting a biomaterial of claim 9, wherein the specific binding between the capture molecule and the target molecule is selected from the group consisting of nucleic acid hybridization and enzyme binding reaction.

15. The apparatus for detecting a biomaterial of claim 9 wherein the nucleic acid comprises at least one selected from the group consisting of RNA, PNA, LNA, and a hybrid thereof.

16. The apparatus for detecting a biomaterial of claim 9, wherein the protein comprises at least one selected from the group consisting of enzyme, matrix, antibody, ligand, aptamer, and receptor.

17. The biochip of claim 1, wherein the substrate is formed of cyclic olefin copolymer (COC).

18. The biochip of claim 1, wherein the metal thin film is formed of Au,
  wherein the spacer is formed of an organic material,
  wherein the capture molecules are immobilized by carboxyl (—COOH), which are induced on the surface of the spacer, and
  wherein the fluorophore comprises a Europium ($Eu^{3+}$).

19. The apparatus for detecting a biomaterial of claim 9, wherein the specific binding between the capture molecule and the target molecule comprises an antigen-antibody reaction,
  wherein the capture molecule comprises a nucleic acid or a protein,
  wherein the nucleic acid comprises DNA, and
  wherein the protein comprises an antigen.

* * * * *